United States Patent
Martin et al.

[11] Patent Number: 6,083,002
[45] Date of Patent: Jul. 4, 2000

[54] CARTRIDGE FOR DISPENSING LIQUID COMPOSITIONS

[75] Inventors: Thomas W. Martin, Little Canada; John M. Horn, Woodbury, both of Minn.

[73] Assignee: 3M Innovative Properties Co., St. Paul, Minn.

[21] Appl. No.: 09/244,197

[22] Filed: Feb. 4, 1999

[51] Int. Cl.⁷ .................................................. A61C 5/04
[52] U.S. Cl. ........................ 433/90; 433/89; 604/236; 604/310
[58] Field of Search ................... 433/90, 89; 604/1, 604/236, 2, 310, 311; 401/240, 176, 286, 129, 171; 222/386, 132, 137, 92; 15/221

[56] References Cited

U.S. PATENT DOCUMENTS

| | | | |
|---|---|---|---|
| 3,369,543 | 2/1968 | Ronco | 604/2 |
| 3,519,364 | 7/1970 | Truhan | 401/177 |
| 3,792,699 | 2/1974 | Tobin et al. | 128/2 W |
| 3,918,435 | 11/1975 | Beall et al. | 128/2 W |
| 3,924,623 | 12/1975 | Avery | 128/269 |
| 3,938,898 | 2/1976 | Reitknecht | 401/183 |
| 4,198,756 | 4/1980 | Dragan . | |
| 4,225,254 | 9/1980 | Holberg et al. | 401/119 |
| 4,391,590 | 7/1983 | Dougherty . | |
| 4,472,141 | 9/1984 | Dragan . | |
| 4,578,055 | 3/1986 | Fischer | 604/2 |
| 4,767,326 | 8/1988 | Bennett et al. . | |
| 4,969,816 | 11/1990 | Drumm | 433/90 |
| 5,100,320 | 3/1992 | Martin et al. . | |
| 5,125,836 | 6/1992 | Dragan et al. | 433/90 |
| 5,246,371 | 9/1993 | Fischer | 433/217 |
| 5,267,859 | 12/1993 | Discko, Jr. | 433/89 |
| 5,269,684 | 12/1993 | Fischer | 433/90 |
| 5,306,147 | 4/1994 | Dragan et al. | 433/90 |
| 5,336,088 | 8/1994 | Discko, Jr. | 433/90 |
| 5,624,260 | 4/1997 | Wilcox et al. | 433/90 |
| 5,816,804 | 10/1998 | Fischer | 433/90 |

FOREIGN PATENT DOCUMENTS

| | | | |
|---|---|---|---|
| WO 97/26041 | 7/1997 | WIPO | A61M 37/00 |
| WO99/18880 | 4/1999 | WIPO . | |

*Primary Examiner*—Gene Mancene
*Assistant Examiner*—Pedro Philogene
*Attorney, Agent, or Firm*—James D. Christoff

[57] ABSTRACT

A dispensing cartridge especially suitable for use with a hand-held applicator for dispensing liquids having a relatively low viscosity has a chamber and at least one compressible, porous material received in the chamber. Each of the porous materials receives a quantity of a liquid composition. As a piston is advanced in the chamber, each porous material is compressed to cause the composition or compositions to be discharged through an outlet opening.

39 Claims, 2 Drawing Sheets

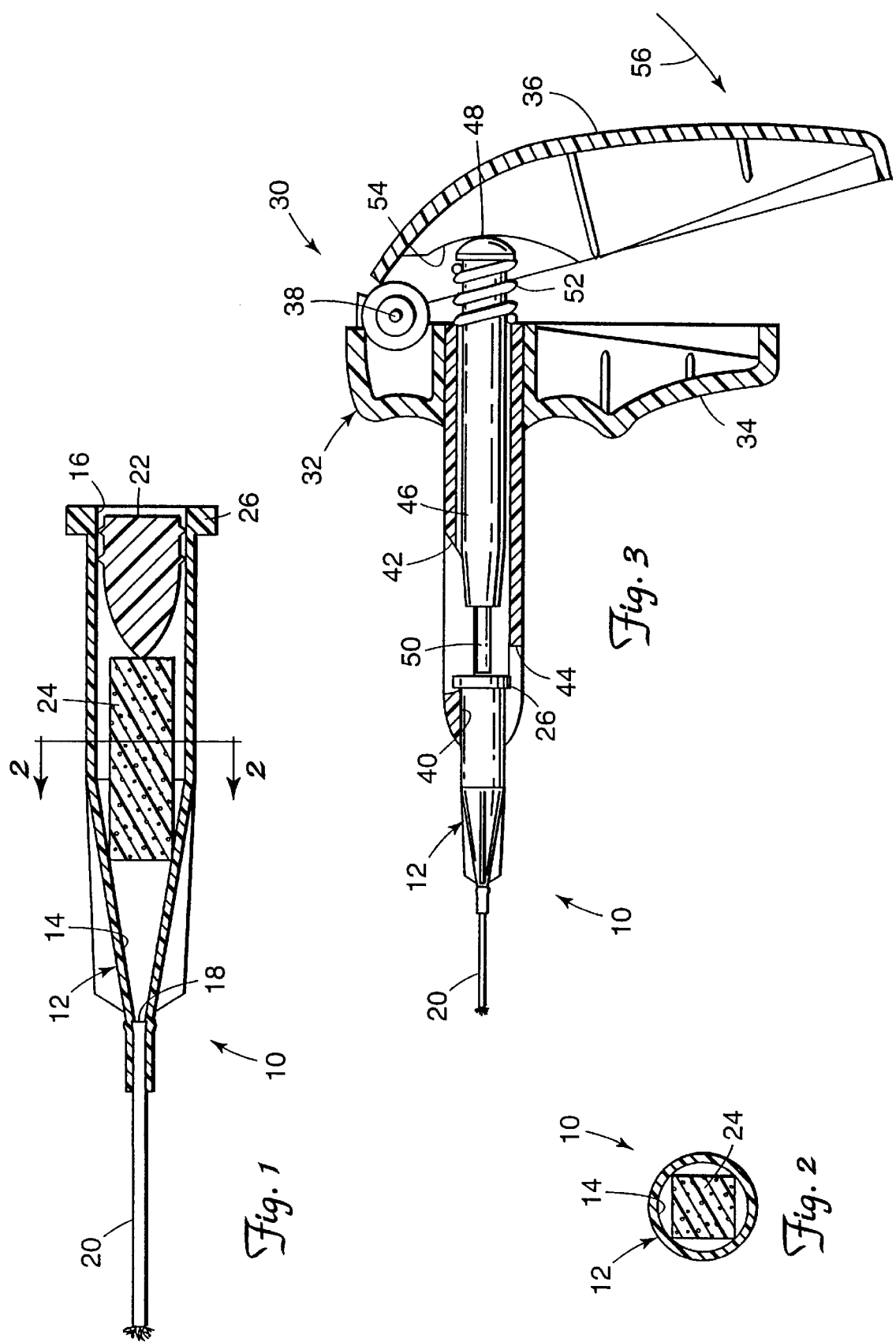

CARTRIDGE FOR DISPENSING LIQUID COMPOSITIONS

BACKGROUND OF THE INVENTION

1. Field of the Invention

The field of the present invention relates to a disposable dispensing cartridge of the type adapted to be releasably received in an applicator having a movable plunger. More particularly, the field of the present invention is directed to a disposable dispensing cartridge that is especially suitable for dispensing liquid compositions having a relatively low viscosity.

2. Description of the Related Art

A number of dispensing devices are available for dispensing various types of materials. In many instances, the dispensing device is an assembly that includes a reusable dispenser or applicator and a disposable cartridge. The cartridge contains a quantity of a composition or material to be dispensed and is releasably received in a receptacle of the applicator.

In some dispensing assemblies that include an applicator and a cartridge, the applicator has a plunger that is advanced by the user during a dispensing operation. Often, the plunger is received in an open end of the cartridge and bears against a piston within the cartridge. As the plunger is advanced to move the piston, the piston expels a quantity of material through a front outlet opening of the cartridge.

Dispensing devices that include a reusable applicator and a disposable cartridge are favored in many instances, especially in instances where the applicator is relatively expensive in comparison to the cost of the cartridge. For example, many applicators have a movable lever or arm for facilitating advancement of the plunger. Some applicators have a ratchet mechanism associated with the lever for enhancing control over movement of the plunger. Obviously, it is desirable to reuse such applicators in order to reduce costs and avoid disposal issues.

Dispensing devices with disposable cartridges are often used in the field of dentistry for dispensing dental compositions such as restoratives, adhesives, cements, etching gels, sealants and the like. In some instances, the cartridge and the front portion of the applicator receiving the cartridge are relatively small so that the cartridge can be readily maneuvered in the oral cavity during a dispensing operation. In that manner, the dental material contained in the cartridge may be conveniently dispensed directly onto the tooth structure as needed.

Examples of hand-held applicators (also called dispensers or ejector-type guns) that have been used in dentistry are described in U.S. Pat. Nos. 4,198,756, 4,391,590 and 4,472,141. Examples of cartridges (also known as capsules) useful with those applicators are described, for example, in U.S. Pat. Nos. 4,391,590, 4,767,326, 5,100,320 and 5,624,260.

In the field of dentistry, dispensing cartridges are often relatively small and adapted to be used with a single patient. The cartridge is disposed of after the procedure has been accomplished and the applicator is disinfected before use with another cartridge for a subsequent patient. In this manner, the risk of transferring an infectious disease from one patient to another is substantially reduced.

Many of the dental applicators and disposable cartridges that are presently commercially available are used to dispense relatively thick, semi-liquid compositions having a medium or mid-range viscosity ranging from, for example, the viscosity of mayonnaise to a stiff putty. The dental hand-held applicators described in the patents mentioned above include a movable lever that provides a substantial mechanical advantage over movement of the plunger which, in turn, is sufficient to advance the piston in the cartridge and force the composition in the cartridge through a relatively small outlet opening. The substantial mechanical advantage provided by the lever of the applicator is an advantage in those circumstances, because it enables the dental practitioner to dispense the composition directly to a precise location in the oral cavity without undue effort and by use of only one hand.

Unfortunately, the dental applicators and disposable cartridges mentioned in the preceding paragraph are not satisfactory for use in dispensing liquid compositions having a relatively low viscosity such as a viscosity similar to the viscosity of water or milk. In dispensing compositions having relatively low viscosities, the mechanical advantage provided by the applicators mentioned above greatly hinders precise control over the amount of material discharged from the cartridge, since a slight movement of the piston may result in squirting of the composition out of the cartridge. As can be appreciated, such lack of control in dental procedures represents a significant disadvantage that is best avoided.

As a result, it has become common practice for dental practitioners to select some other type of applicator and dispensing method for dispensing dental compositions having a relatively low viscosity. Often, such compositions are dispensed into a mixing well from a squeezable vial, from a syringe or from another type of applicator, such as the applicator shown in applicant's U.S. Pat. No. 5,735,437. In those instances, it is common practice for the practitioner to use a small brush, swab or other similar device to transfer the composition from the mixing well to the patient's dental structures (i.e., the patient's teeth and/or gingiva).

However, the use of the mixing well and brush or swab device as described in the previous paragraph is not entirely satisfactory, in that the steps of dispensing the composition into the well and then transferring the composition from the well to the patient's dental structure is more time-consuming than the act of simply dispensing the liquid composition from a container directly onto the patient's dental structure. Also, there is a risk that the composition may drop off of the brush or swab during conveynance between the well and the dental structure. In addition, the brush or swab device and often the mixing well are intended for use with only a single patient, presenting an issue of disposal. Furthermore, there is a slight risk that the composition may be contaminated and/or contacted by the practitioner while sitting in the open well.

As a consequence, there is a need in the art for a new system that is especially adapted for dispensing precise quantities of compositions having a relatively low viscosity. Preferably, such a system would be useful in the dental arts so that liquid compositions may be dispensed directly onto the teeth and/or gingiva of a dental patient if desired. Moreover, it would be beneficial for such systems to be usable with conventional, well-known applicators so that the operator may dispense the composition and use the applicator with familiar techniques.

SUMMARY OF THE INVENTION

The present invention is directed to a dispensing cartridge that is particularly useful for dispensing liquid compositions having a relatively low viscosity using, as an option, a conventional hand-held applicator. The dispensing cartridge has a chamber with at least one compressible, porous material bearing one or more liquid compositions. As a piston advances in the chamber, each porous material is compressed and the liquid composition or compositions are dispensed through an outlet opening.

In more detail, the present invention in one aspect is directed toward a dispensing cartridge for use with a hand-held applicator. The dispensing cartridge includes a body having an open end for receiving a plunger of an applicator. The body also includes an outlet opening and a chamber extending between the open end and the outlet opening. A piston is slidably received in the chamber, and a compressible, porous material is received in the chamber. A liquid composition is received by the porous material. The liquid composition is urged toward the outlet opening as the piston is advanced in the chamber and compresses the porous material.

Another aspect of the present invention is also directed toward a dispensing cartridge for use with a hand-held applicator. In this aspect, the cartridge includes a body having an open end for receiving a plunger of an applicator, and the body also includes an outlet opening and a chamber extending between the open end and the outlet opening. A piston is slidably received in the chamber. A first compressible, porous material is received in the chamber and a second compressible, porous material is received in the chamber. A first liquid composition is received by the first porous material, and a second liquid composition that is different than the first liquid composition is received by the second porous material. The first liquid composition and the second liquid composition are urged toward the outlet opening as the piston is advanced in the chamber and compresses the first porous material and the second porous material.

Another aspect of the present invention is directed toward a method of dispensing a dental composition. The method includes the act of providing a cartridge having a chamber and a porous material received in the chamber, wherein the porous material receives a quantity of liquid composition. The method also includes the act of advancing a piston in the chamber to compress the porous material and urge the liquid composition from the porous material and toward an outlet opening.

An additional aspect of the present invention is also directed toward a method of dispensing a dental composition. In this aspect, the method includes the act of providing a cartridge having a chamber, a first porous material received in the chamber and a second porous material received in the chamber, wherein the first porous material receives a quantity of a first liquid composition and wherein the second porous material receives a quantity of a second liquid composition that is different than the first liquid composition. The method also includes the act of advancing a piston in the chamber to compress the first porous material and the second porous material and urge the first liquid composition and the second liquid composition toward an outlet opening.

The present invention is particularly advantageous, in that the porous material provides precise control over dispensing of the composition or compositions even in instances where each composition has a relatively low viscosity similar to the viscosity of water. Dispensing of relatively small amounts of a composition or compositions can be carried out at a precise location, and as such the invention is particularly useful in the field of dentistry for applying one or more compositions directly onto the tooth structure or gingiva of a dental patient. Additionally, the invention can be carried out with conventional, well-known applicators with which the user is familiar and may already have in his or her possession.

Other aspects, features and benefits of the present invention are set out in the detailed description that follows and are illustrated in the accompanying drawings.

BRIEF DESCRIPTION OF THE DRAWINGS

FIG. 1 is a side cross-sectional view of a dispensing cartridge constructed according to one embodiment of the invention;

FIG. 2 is an end cross-sectional view of the cartridge illustrated in FIG. 1 and taken along lines 2—2 of FIG. 1;

FIG. 3 is a reduced side cross-sectional view of a hand-held applicator along with the dispensing cartridge of FIGS. 1 and 2, wherein the dispensing cartridge is received in a receptacle of the applicator for use in a dispensing operation;

DETAILED DESCRIPTION OF THE PREFERRED EMBODIMENTS

Figure 4:
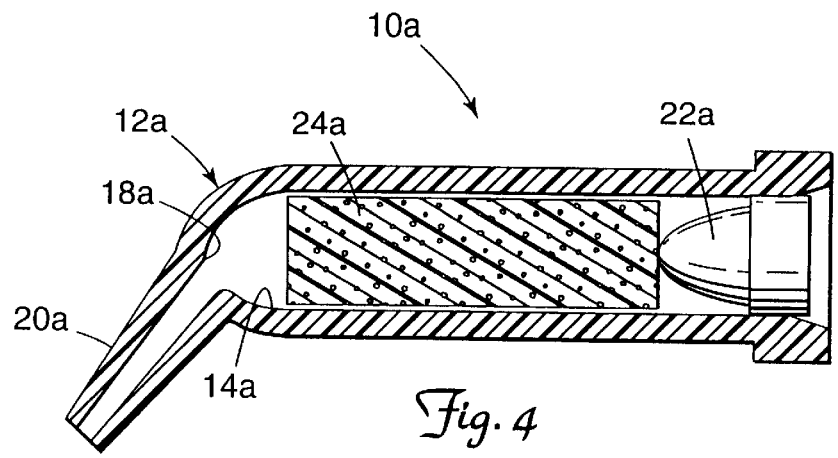
FIG. 4 is a side cross-sectional view of a dispensing cartridge constructed according to another embodiment of the invention.

An example of a dispensing cartridge constructed in accordance with the principles of the present invention is illustrated in FIGS. 1 and 2 and is broadly designated by the numeral 10. The cartridge 10 includes a body 12 having a chamber 14. The body 12 and the chamber 14 are both elongated and preferably have circular cross-sections when taken in directions perpendicular to their collinear, central longitudinal axes.

The body 12 includes an open inlet end 16 and an outlet or outlet opening 18 that is remote from the open end 16. In this embodiment, the outlet opening 18 is located at one end of a passage that extends through an elongated discharge nozzle 20. The discharge nozzle 20 is preferably made of a metal cannula that is sufficiently bendable upon the application of finger pressure so that the user can readily bend the nozzle 20 to a particular angle or configuration as desired.

Preferably, the discharge nozzle 20 is rotatable relative to the body 12 to facilitate precisely dispensing a composition or compositions at a particular location, such as a location in the oral cavity. Optionally, the rear end of the nozzle 20 is flared and forcibly embedded in an internal wall portion of the body 12 surrounding the outlet opening 18 in order to substantially preclude the discharge nozzle 20 from being forced outwardly during dispensing and also from being moved rearwardly into the chamber 14. Optionally, the discharge nozzle 20 and the method of assembling the nozzle 20 to the body 12 are similar to the nozzles and methods described in U.S. Pat. No. 5,336,088, which is expressly incorporated by reference herein.

Preferably, the outer end of the nozzle 20 includes a liquid application mechanism by which liquid composition can be applied. The liquid application mechanism has the capability to retain or suspend a small quantity of liquid composition at and at least partially about the exterior of the nozzle end after it has been dispensed through the nozzle passage so that the liquid composition can be applied to an application site.

The liquid application mechanism also advantageously disperses liquid composition within itself and about at least some of the surface area of the nozzle 20 for application of liquid composition by a greater portion of the nozzle 20 than just its outer end opening.

In the embodiment shown in FIGS. 1 and 2, the liquid application mechanism comprises a plurality of small, flocked fibers extending outwardly from the end of the nozzle 20. The flocked fibers are beneficial for applying a liquid dental composition to the surface of a tooth, and in particular for applying such a liquid composition within a cavity prepared in a tooth, i.e. to fit within the prepared cavity. This ability may also be modified by the length of the flocked fibers. A flocked fiber tip can be made by any known or developed technique, such as is done in making the flocked tip disposable applicators that are commercially available from Microbrush Corporation of Clearwater, Fla. under the trade designation "Microbrush." The flocked fibers define small interstitial spaces that can advantageously fill with liquid composition. Those spaces retain and suspend a small amount of liquid composition after it has been dispensed through the opening at the outer end of the nozzle 20 to provide for efficient application of the liquid composition to a preparation site. The fibers also allow relatively uniform application of the liquid composition over the surface(s) of the preparation site, whether irregular, rough or smooth, and apply liquid composition in the same way as a brush would.

It is also contemplated that the liquid application mechanism could be formed in other ways and be comprised of other materials. Bristles can be secured at the end of the nozzle 20 in any conventional or developed way, but should be arranged to disperse and suspend liquid material in accordance with the present invention. The bristles may be conventional in the sense of those that are suitable for paint brush type applicators. Another type of liquid application mechanism would be a liquid dispersing material, such as an open cell foam or woven or nonwoven fabrics such as felt (e.g., as used in felt tip markers), covering at least a part of the nozzle 20. Liquid composition could enter the open cell foam or other material from the nozzle outlet and disperse therein for application. That is, as with the flocked fibers and brushes noted above, such other materials should preferably be able to retain or suspend a small quantity of liquid composition outside of the nozzle end to facilitate application by more than just the area surrounding the nozzle outlet. Resilient mechanisms (made up of multiple elements like fibers or bristles or of liquid dispersing material like open cell foam) are preferred in that they have the added ability to conform and apply liquid composition to an irregular surface. Moreover, multiple mechanisms can be used together to cover various portions of a tip or in combination over one another.

A piston 22 is slidably received in the chamber 14, and is movable in a direction along the longitudinal axis of the chamber 14 toward the outlet opening 18. The piston 22 in this embodiment has a bullet-like configuration with a tapered front end portion and a flat rear wall. The piston 22 has a circular configuration when viewed in sections that are perpendicular to the longitudinal axis of the chamber.

Preferably, the outer diameter of the piston 22 is approximately the same as the inner diameter of the chamber 14 in order to provide a seal between the piston 22 and the body 12 as the piston 22 is advanced. Optionally, the piston 22 may be provided with small circumferential fins to enhance the seal between the internal walls of the body 12 defining the chamber 14 and the external side walls of the piston 22.

As a further option, the front end portion of the piston 22 may have a shape complemental to inner wall portions of the body 12 surrounding a front end portion of the chamber 14 so as to facilitate maximum evacuation of composition(s) from the chamber 14 when the piston 22 is fully advanced.

A compressible, porous material 24 having a number of small pores is received in 25 the chamber 14 between the piston 22 and the front end of the chamber 14. Preferably, but not necessarily, the porous material 24 includes not only closed-end pores but also includes a number of small internal passageways that intersect and communicate with one another (i.e., has an open cellular construction). Preferably, the internal passageways are orientated in different directions and extend from one side to the other.

Examples of suitable porous materials 24 include foams and sponges. An example of a suitable foam material is an open cell, thermo-reticulated polyurethane foam, such as is available from Wilshire Foam Products. Other flexible cellular plastic foam materials include rubber latex, polyethylene and vinyl polymers. In some instances, rigid foams may be used, such as polystyrene, polyurethane, epoxy and polyvinyl chloride. For additional information on these and other suitable foams, the reader is referred to the article entitled, "Foamed Plastics", Vol. 11, p. 730 et. seq., *Kirk-Othmer's Encyclopedia of Chemical Technology*, Fourth Edition (1994) which is incorporated by reference. Preferably, but not necessarily, the porous material 24 is resilient and possesses an inherent memory, such that it returns to its normal shape after a compressing force is removed.

Other suitable materials for the porous material include non-plastic foams and sponges. In some instances, ceramic or metallic foams may be used. Other materials also include blown fibers, and synthetic or natural batting, stuffing, wadding or gauze (such as cotton wadding or gauze).

A liquid composition is received and preferably retained by the porous material 24. The porous material 24 is selected from a material that is compatible with the liquid composition, and preferably is selected from a material that has an affinity for the liquid composition in order to facilitate reception and retention of the liquid composition in the various pores and passageways. The affinity enables the porous material 24 to spontaneously absorb and draw into the pores, without compression, the liquid composition. Preferably, the porous material 24 is inert to the liquid composition.

Affinity between the liquid composition and the porous material 24 may be provided by interfacial forces, by chemical attraction and/or by any other suitable phenomena (including hydrophilicity). Interfacial forces include surface forces or surface tension forces that govern wetting of the porous material 24 by the liquid composition. Chemical attraction may be provided by, for example, hydrogen bonding depending upon the identity of the porous material 24 and the liquid composition. Optionally, the liquid composition may contain a surfactant or other agent that enhances the affinity.

As the piston 22 is advanced in the chamber 14 in a direction toward the outlet opening 18, the front end of the piston 22 bears against the porous material 24 such that the porous material is compressed between the piston 22 and the front wall portions of the chamber 14. As the piston 22 continues to advance, liquid composition in the porous material is urged from the pores and/or passageways and moves generally in a direction toward the outlet opening 18. Continued advancement of the piston 22 directs the liquid composition through the discharge nozzle 20 and to an application site as selected by the user.

The length of the porous material 24 relative to the length of the chamber 14 may vary from that shown in FIG. 1 in accordance to the expected volume of liquid composition to be received by the porous material 24. For example, a longer section of a porous material, possibly extending from the piston 22 to the outlet opening 22, may be desired in some instances, such as when the liquid composition is a sealant that is intended for application to all of the patient's teeth. In those instances, the front end section of the porous material 24 may be trimmed to a taper to match the shape of the front end portion of the chamber 14, or alternatively simply compressed and forced in place. Optionally, but not necessarily, the porous material 24 shifts in the chamber 14 in a direction toward the outlet opening 18 as the piston 22 is advanced.

Preferably, the porous material 24 has a cross-sectional area that is smaller than the cross-sectional area of the chamber 14 in directions transverse to the longitudinal axis of the chamber 14. A number of cross-sectional shapes for the porous material 24 are possible, including cylindrical, triangular, truncated triangular, rectangular and the like. Preferably, the porous material 24 has a rectangular configuration and more preferably has a square configuration in directions transverse to the longitudinal axis of the chamber 14 as is shown in FIG. 2. The rectangular or square cross-sectional configuration is an advantage in that the porous material 24 can be easily made by cutting a box-like small section of porous material from a larger, flat sheet of porous material, such as the sheets of porous material that are commercially available. As a result, the potentially more difficult task of cutting small cylindrical sections of the porous material or sections of other configurations is avoided.

The square cross-sectional configuration of the porous material 24 also presents an advantage during manufacture of the cartridge 10, since the square configuration provides four air spaces along the four longitudinal sides of the porous material 24. For example, once the porous material 24 has been placed in the chamber 14 during manufacture of the cartridge 10, the liquid composition can be introduced into the porous material 24 by moving a rigid dispensing tube through the open end 16 and placing the tube in contact with the rear side of the porous material 24. The liquid composition can then be directed through the tube and introduced into the porous material 24, preferably facilitated by the affinity between the liquid composition and the porous material 24 as mentioned above. As the liquid composition fills the passageways in the porous material 24, the air spaces along the sides of the porous material 24 provide a vent for the escape of air if necessary.

During the filling operation as mentioned above, the affinity between the porous material 24 and the liquid composition is a further advantage in that the affinity reduces the need to cover or plug the discharge nozzle 24 during the filling operation. The affinity as mentioned above assures that the porous material 24 retains the liquid composition in its pores and passageways until such time as the porous material is compressed. Moreover, the affinity between the porous material 24 and the liquid composition reduces the need and in some instances may eliminate the need to provide a shipping cap for the discharge nozzle 20, a particular advantage when the end of the discharge nozzle 20 is flocked or has other fibrous material to enhance dispensing of the liquid composition. In instances where no cap is needed to retain the liquid composition in the chamber 14, the cartridge 10 may be packaged in a foil pouch or other container to avoid contamination and/or undue premature exposure of the composition to the atmosphere.

The cartridge body 12 also includes a rear flange 26 that circumscribes the open end 16. The rear flange 26 is useful for retaining the cartridge 10 in an applicator, such as the applicator described below. Optionally, the open end 16 includes a chamfered portion that leads to the chamber 14 to facilitate insertion of the piston 22 during assembly of the cartridge 10. As another option, a rear external wall of the rear flange 26 is chamfered, although as an alternative the rear flange 26 could have a 90-degree rear outer corner if desired.

An example of a dispensing device useful for dispensing liquid composition from the cartridge 10 is a hand-held applicator such as the applicator 30 shown in FIG. 3. The applicator 30 as illustrated is identical to well-known applicators used in the dental field (such as 3M's dental applicator no. 5706SD) and includes a housing 32 with a depending handle 34. A rear lever 36 of the applicator 30 is connected to the housing 32 by a pivot 38 for swinging movement about a horizontal reference axis when the handle 34 extends in a vertical direction.

The front of the housing 32 includes a tubular projection having an internal cylindrical receptacle 40 for releasably receiving the cartridge 10. When the cartridge 10 is received in the receptacle 40, the cartridge 10 extends through a circular opening located at the front end of the housing 32. The circular opening has a diameter that is somewhat larger than the outer diameter of the body 12 in areas in front of the rear flange 26. However, the circular front opening of the housing 32 has a diameter that is somewhat smaller than the outer diameter of the rear flange 26 in order to retain the cartridge 10 in the receptacle 40 during a dispensing operation.

The front tubular projection of the housing 32 also includes an upper opening 42 adjacent the receptacle 40 for inserting the cartridge 10 in the receptacle 40 or removing the cartridge 10 from the receptacle when desired. The confined opening 42 is located laterally of the receptacle 40. The applicator 30 is sometimes known as a "breech-loading" applicator.

Preferably, the front tubular projection of the housing 32 includes a lower elongated slot 44. The slot 44 extends from the front end of the housing 32 and is adjacent the receptacle 40. The slot 44 conveniently provides additional clearance for the front of the cartridge 10 including the discharge nozzle 20 when the cartridge 10 is inserted into or moved from the receptacle 40.

The applicator 30 includes an elongated plunger 46 with a rear, somewhat semi-spherical enlarged head 48. The plunger 46 also includes an elongated cylindrical shaft 50 that is preferably made of a relatively strong, wear-resistant material such as stainless steel. As shown in FIG. 3, a coiled compression spring 52 surrounds the plunger 46 and is located between the head 48 and the rear opening of a passageway that extends through the tubular projection of the housing 32 and leads to the receptacle 40.

A drive means of the applicator 30 includes a pair of curved cam surfaces 54, one of which is illustrated in FIG. 3. The cam surfaces 54 are formed on an upper, inner portion of the lever 36 and are orientated for sliding engagement with the curved surface of the plunger head 48. As the lever 36 is moved in an arc about the pivot 38 in the direction of the arrow designated by the numeral 56, the head 48 rides along the cam surfaces 54 and moves the plunger 46 in a forward direction toward the cartridge 10 when the cartridge 10 is received in the receptacle 40.

The outer diameter of the shaft 50 is somewhat smaller than the diameter of the open end 16 of the cartridge 10. As the lever 36 is pivoted in the direction of the arrow 56 and the plunger 46 is advanced toward the cartridge 10, the shaft 50 enters the open end 16 and bears against the rear wall of the piston 22. Continued advancement of the lever 36 in the direction of the arrow 56 moves the piston 22 forwardly, whereupon the front portion of the piston 22 exerts a compressive force on the porous material 24.

As the porous material 24 is compressed, the space within the pores and the passageways of the porous material is reduced such that the liquid composition is urged out of the porous material 24. As the rear lever 36 continues to move in the direction of the arrow 56 to advance the piston 22, the liquid composition is urged in a direction generally toward the outlet opening 18 and through the passageway of the discharge nozzle 20. Additional movement of the rear lever 36 in the direction of the arrow 56 advances the piston 22 until the latter has reached its limit of travel in a forward direction, at which time the porous material 24 is preferably essentially fully compressed.

Preferably, the porous material 24 is highly compressible, so that the liquid composition is substantially depleted from the pores and passageways of the porous material 24 when the piston 22 is fully advanced without undue effort on the lever 36. Use of a highly compressible porous material 24 is also an advantage in that such materials tend to dispense a greater quantity of composition than materials that are not as compressible by comparison.

Preferably, however, the porous material 24 is not completely saturated with the liquid composition when the cartridge 10 is assembled so that some amount of air space remains in the pores and passageways of the porous material 24. In this manner, the liquid composition is not immediately dispensed from the discharge nozzle 20 when the rear lever 36 is initially moved, even though such movement of the lever 36 may advance the piston 22 and begin to compress the porous material 24. Such initial compression of the porous material 24 without dispensing of the liquid composition advantageously provides tactile feedback to the user, so that the user can assess the degree of force necessary to advance the piston 22 and adjust the force as necessary during initial stages of movement of the rear lever 36 in order to better control the flow rate of liquid composition once the composition begins to flow from the nozzle 20.

The body 12 and the piston 22 may be made of any suitable material, including plastic materials. An example of a suitable plastic material for the body 12 and the piston 22 is polypropylene. Another example of a suitable material for the body 12 is a nylon resin such as Zytel brand nylon resin, no. 101L from DuPont. Other examples of suitable materials for the body 12 are described in U.S. Pat. Nos. 5,624,260 and 5,100,320, both of which are incorporated by reference herein.

Optionally, the body 12 is made of a material that transmits light in at least a portion of the visible wavelengths, so that the operator can observe the compression of the porous material 24 within the chamber 14 and advancement of the liquid composition toward the discharge nozzle 20. If the liquid composition is photocurable, the body 12 is preferably substantially opaque to actinic radiation, while optionally allowing passage of light in at least some of the visible wavelengths to permit observation of the chamber 14.

Another embodiment of the invention is illustrated in FIG. 4, wherein a cartridge 10a includes a body 12a, a piston 22a received in a chamber 14a of the body 12a, and a porous material 24a received in the chamber 14a. A liquid composition is received by the porous material 24a. Except as set out below, the various elements and aspects of the cartridge 10a are identical to the elements and aspects of the cartridge 10 as described above.

A discharge nozzle 20a of the cartridge 10a extends at an angle relative to the longitudinal axis of the chamber 14a. The discharge nozzle 20a is integrally connected to the body 12a and has a passage that communicates with an outlet opening 18a. Preferably, the outer end of the nozzle 20a includes a liquid application mechanism as described above. Inner wall portions of the body 12a surrounding the front-end portion of the chamber 14 are curved and tapered and optionally match the shape of a tapered front end portion of the piston 22a. The operation and resulting advantages of the cartridge 10a are essentially the same as the operation and advantages of the cartridge 10 described above.

Figure 5:
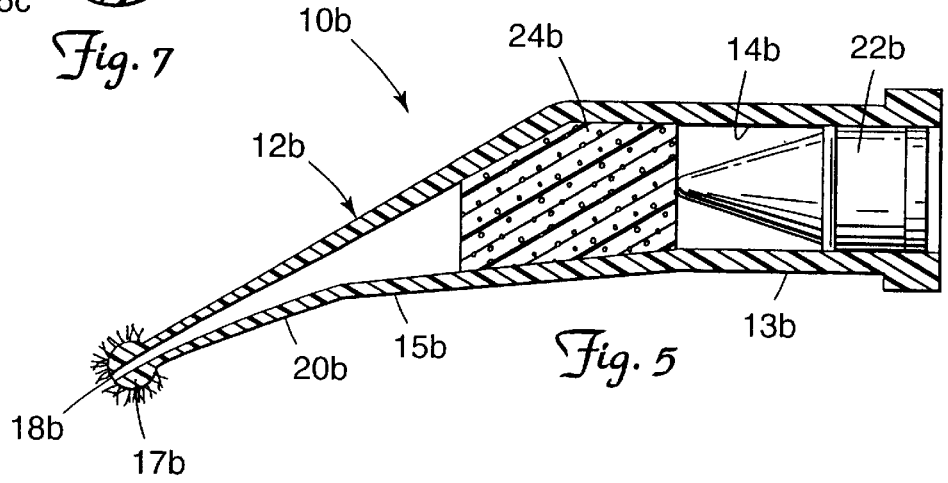
FIG. 5 is a side-cross sectional view of a dispensing cartridge according to yet another embodiment of the invention.

A cartridge 10b according to another embodiment of the invention is shown in FIG. 5 and includes a body 12b having a chamber 14b, a piston 22b and a porous material 24b. Except as described below, the various elements and aspects of the cartridge 10b are essentially identical to the corresponding elements and aspects of the cartridge 10 as set out above.

The body 12b includes a rear cylindrical section 13b as well as a front, somewhat conical section 15b that is integrally joined at an angle to the cylindrical section 13b. The conical section 15b integrally tapers to a narrow discharge tip or nozzle having an outlet opening 18b. In this embodiment, the cannula as described above in connection with the cartridge 10 is omitted.

Preferably, a front-end portion of the conical section 15b includes a ball-shaped tip portion 17b through which an outlet passage extends. Preferably, the tip portion 17b is flocked or covered with fibers, bristles or other liquid application mechanism such as described above. The liquid application mechanism aids in spreading and placing the liquid composition on a particular surface, such as the surface of a dental patient's tooth structure or gingiva.

Cartridges of other configurations may also be employed. For example, the cartridge of the present invention may have a configuration such as described in U.S. Pat. Nos. 5,624, 260 and 5,100,320 as mentioned above.

Figure 7:
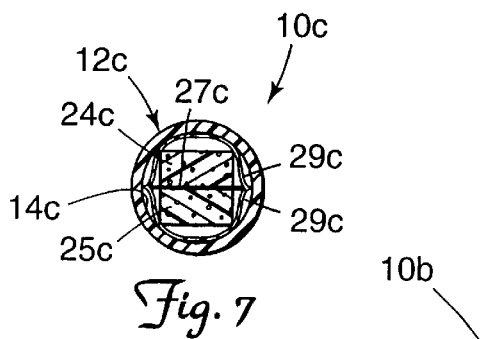
FIG. 7 is an end cross-sectional view of the dispensing cartridge depicted in FIG. 6 and taken along lines 7—7 of FIG. 6.
Figure 6:
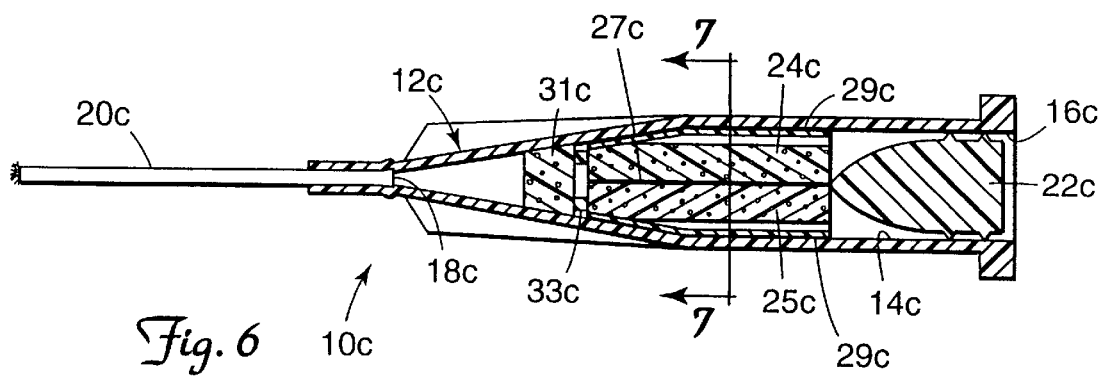
FIG. 6 is a side cross-sectional view of a dispensing cartridge according to still another embodiment of the present invention.

A dispensing cartridge 10c constructed in accordance with another embodiment of the invention is depicted in FIGS. 6 and 7. The cartridge 10c includes a body 12c having a chamber 14c, an open end 16c and an outlet opening 18c. A discharge nozzle 20c is connected to the body 12c, and a piston 22c is slidably received in the chamber 14c. The body 12c, the discharge nozzle 20c and the piston 22c in this embodiment are identical to the body 12, the discharge nozzle 20 and the piston 22 respectively.

The cartridge 10c includes two distinct porous materials 24c, 25c. Optionally, the porous materials 24c, 25c are located alongside each other, and have essentially identical, rectangular, box-like configurations. Each of the porous materials 24c, 25c is made of a material similar to the porous material 24 described above.

The first porous material 24c receives a quantity of a first liquid composition, and the second porous material 25c receives a quantity of a second liquid composition that is preferably different than the first composition. Preferably, a barrier 27c extends between the porous materials 24c, 25c so that the porous materials 24c, 25c do not contact each other before a dispensing operation.

Optionally, the cartridge 10c includes a pair of flexible side panels 29c. A first side panel 29c extends around the porous material 24c and is joined along two edge sections to opposite edge sections of the barrier 27c. A second side panel 29c extends around the porous material 25c and is also joined along two edge sections to opposite edge sections of the barrier 27c.

The barrier 27c and the side panels 29c are preferably made of a suitable flexible material that is compatible with the liquid composition retained in the adjacent porous material 24c or 25c. The barrier 27c and the side panels 29c are sufficiently flexible so that advancement of the piston 22c is not unduly hindered. Suitable materials include, for example, plastic sheet materials such as polyethylene. The side panels 29c may be fixed to the barrier 27c by an adhesive, by an ultrasonic welding process or by a heat sealing operation.

Preferably, the cartridge 10c also includes a mixing element 31c. The mixing element 31 c is preferably located in the chamber 14c between the outlet opening 18c and the porous materials 24c, 25c. The mixing element may be constructed of any suitable material having a structure or configuration that effectively mixes the first and second liquid compositions as the liquid compositions are moved through the chamber 14c to the outlet opening 18c.

Suitable materials for the mixing element 31c include, for example, the same materials described above in connection with the porous material 24. The mixing element 31c preferably has numerous internal passageways that intimately mix the two liquid compositions together during passage toward the outlet opening 18c. As an alternative, the mixing element 31c may have a series of molded blades, vanes or other structure that serves to intimately mix the liquid compositions together during passage toward the outlet opening 18c.

The barrier 27c and the side panels 29c preferably do not extend across a rear face of the porous materials 24c, 25c. As such, the liquid compositions may be delivered to the porous materials 24c, 25c by passing a pair of side-by-side rigid filling tubes through the open end 16c until such time as the tubes each contact the rear face of a respective one of the porous materials 24c, 25c.

Moreover, the barrier 27c and the side panels 29c do not extend across a front face of the porous materials 24c, 25c. As a consequence, the first and second liquid compositions are free to exit the pores and passageways of the porous materials 24c, 25c respectively and pass into the mixing element 31 c when the piston 22c is advanced. The preferred affinity between the porous materials 24c, 25c and the first and second liquid compositions respectively in the manner described above in connection with the cartridge 10 helps to ensure that the first and second liquid compositions do not contact each other or leave the chamber 14c until such time as the porous materials 24c, 25c are compressed.

Preferably, the porous materials 24c, 25c are spaced from the mixing elements 31c in order to hinder unintentional passage of the first and second liquid compositions into the mixing element 31c until the piston 22c is advanced. As one example, a small annular-shaped member 33c may be placed in the chamber 14c between the mixing element 31c and the porous materials 24c, 25c in order to keep the mixing element 31c from contacting the porous materials 24c, 25c before a dispensing operation. Another method that may be used for retaining the mixing element 31c in spaced relationship from the porous materials 24c, 25c is to extend the side panels 29c over the front face of the porous material 24c, 25c and then lightly seal or bond those front extended sections to each other or to the barrier 27c in such a manner that the seal or bond ruptures upon advancement of the piston 22c and allows the first and second compositions to flow into the mixing element 31c. As another option, the side panels 29c could be sufficiently weak to burst open within the front extended sections when the piston 22c is advanced.

The cartridge 10c is particularly useful for dispensing two part compositions that cure or otherwise react with each other once mixed. For example, the first and second liquid compositions may represent a part A and part B of an adhesive that begins to harden once the parts A, B contact each other. Examples of suitable two part compositions useful with the cartridge 10c in dental procedures include Scotchbond dual cure dental adhesives (no. 7535) and Concise white sealant (no. 1910), both from 3M Company.

The cartridges as described in the various embodiments above are particularly useful for dispensing low viscosity dental compositions such as adhesives, etchants, sealants and the like. The cartridges are relatively inexpensive and can be conveniently disposed of after use for a single patient. However, the cartridges as described above may also be used to dispense non-dental compositions such as adhesives or other materials for household, industrial, medical or other applications.

Moreover, the cartridges of the invention may be used with applicators other than the applicator 30 illustrated in FIG. 3. For example, applicators of the type having a side-loading receptacle may be employed. Examples of suitable alternative applicators are described in U.S. Pat. Nos. 4,198,756, 4,391,590, 4,472,141 and 5,743,436.

Those skilled in the art may recognize that various additions and modifications may be made to the presently preferred embodiments that are described in detail above without departing from the spirit of the invention. As a result, the invention should not be deemed limited to the specific embodiments that are set out above, but instead limited only by a fair scope of the claims that follow along with their equivalents.

What is claimed is:

1. A dispensing cartridge for use with a hand-held applicator that provides mechanical advantage comprising:
   a body having an open end for receiving a plunger of an applicator, the body also including an outlet opening and a chamber extending between the open end and the outlet opening;
   a piston slidably received in the chamber;
   a compressible, porous material received in the chamber; and
   a liquid composition received by the porous material, the liquid composition being urged in a direction toward the outlet opening as the piston is advanced in the chamber and compresses the porous material.

2. A dispensing cartridge according to claim 1 wherein the porous material includes a number of internal passageways that communicate with each other.

3. A dispensing cartridge according to claim 2 wherein the porous material is resilient.

4. A dispensing cartridge according to claim 2 wherein the porous material comprises polyurethane.

5. A dispensing cartridge according to claim 1 wherein the chamber has a side wall portion spaced from the porous material in order to provide an air space alongside the porous material.

6. A dispensing cartridge according to claim 1 wherein the chamber is elongated, and wherein the porous material has a cross-sectional area smaller than the cross-sectional area of the chamber in directions transverse to the longitudinal axis of the chamber in order to provide an air space alongside the porous material.

7. A dispensing cartridge according to claim 6 wherein the chamber has a circular configuration in directions transverse to the longitudinal axis of the chamber and wherein the porous material has a rectangular configuration in directions transverse to the longitudinal axis of the chamber.

8. A dispensing cartridge according to claim 7 wherein the porous material has a square configuration in directions transverse to the longitudinal axis of the chamber.

9. A dispensing cartridge according to claim 1 wherein the cartridge includes a discharge nozzle connected to the body with an outer end, and wherein a quantity of fibrous material is connected to the outer end.

10. A dispensing cartridge according to claim 1 wherein the chamber has a longitudinal axis, wherein the cartridge includes a discharge nozzle connected to the body, and wherein the discharge nozzle has a longitudinal axis that extends at an acute angle relative to the longitudinal axis of the chamber.

11. A dispensing cartridge according to claim 1 wherein the body includes a flange that circumscribes the open end for releasably retaining the cartridge in an applicator.

12. A dispensing cartridge according to claim 1 wherein the liquid composition is a dental composition and wherein the porous material comprises a polymeric foam.

13. A dispensing cartridge for use with a hand-held applicator comprising:

a body having an open end for receiving a plunger of an applicator the body also including an outlet opening and a chamber extending between the open end and the outlet opening;

a piston slidably received in the chamber;

a compressible, porous material received in the chamber;

a liquid composition received by the porous material, the liquid composition being urged in a direction toward the outlet opening as the piston is advanced in the chamber and compresses the porous material; and a second compressible, porous material received in the chamber and a second liquid composition received by the second porous material.

14. A dispensing cartridge according to claim 13 and including a barrier extending alongside the second porous material.

15. A dispensing cartridge according to claim 14 and including a mixing element.

16. A dispensing cartridge for use with a hand-held applicator comprising:

a body having an open end for receiving a plunger of an applicator, the body also including an outlet opening and a chamber extending between the open end and the outlet opening;

a piston slidably received in the chamber;

a first compressible, porous material received in the chamber;

a second compressible, porous material received in the chamber;

a first liquid composition received by the first porous material; and a second liquid composition that is different than the first liquid composition and received by the second porous material, the first liquid composition and the second liquid composition being urged toward the outlet opening as the piston is advanced in the chamber and compresses the first porous material and the second porous material.

17. A dispensing cartridge according to claim 16 and including a barrier located between the first porous material and the second porous material.

18. A dispensing cartridge according to claim 17 wherein the barrier is a flexible sheet.

19. A dispensing cartridge according to claim 17 and including a first side panel extending around the first porous material and a second side panel extending around the second porous material.

20. A dispensing cartridge according to claim 19 wherein the barrier has outer side sections that are secured to the first side panel and the second side panel.

21. A dispensing cartridge according to claim 16 wherein the first porous material is located alongside the second porous material.

22. A dispensing cartridge according to claim 1 wherein the first porous material and the second porous material are compressed to approximately the same extent as the piston is advanced.

23. A dispensing cartridge according to claim 16 wherein the chamber has a longitudinal axis, and wherein each of the first porous material and the second porous material has a longitudinal axis that extends in a direction parallel to the longitudinal axis of the chamber.

24. A dispensing cartridge according to claim 23 wherein the chamber has a circular configuration in directions transverse to its longitudinal axis, and wherein the first porous material and the second porous material each have a rectangular configuration in directions transverse to the longitudinal axis of the chamber.

25. A dispensing cartridge according to claim 16 and including a mixing element received in the chamber.

26. A dispensing cartridge according to claim 25 wherein the mixing element is a porous material having a number of internal passageways that communicate with each other.

27. A dispensing cartridge according to claim 26 wherein the mixing element is compressed as the piston is advanced.

28. A dispensing cartridge according to claim 16 wherein the body includes a flange that circumscribes the open end for releasably retaining the cartridge in an applicator.

29. A dispensing cartridge according to claim 16 wherein the first composition and the second composition provide a dental composition when mixed together and wherein the first porous material and the second porous material each comprise a polymeric foam.

30. A method of dispensing a dental composition comprising the acts of:

providing a cartridge having a chamber and a porous material received in the chamber, wherein the porous material receives a quantity of liquid composition; and advancing a piston in the chamber to compress the porous material and urge the liquid composition from the porous material and toward an outlet opening.

31. A method of dispensing a dental composition according to claim 30 and including the act of placing the outlet opening in an oral cavity of a dental patient as the piston is advanced in order to dispense the liquid composition directly onto dental structure.

32. A method of dispensing a dental composition according to claim 30 wherein the act of advancing a piston is carried out by moving a plunger of a hand-held applicator.

33. A method of dispensing a dental composition according to claim 30 wherein the act of providing a cartridge having a chamber and a porous material received in the chamber includes the act of providing a porous material having passageways that extend from one side to another of the porous material.

34. A method of dispensing a dental composition comprising the acts of:
   providing a cartridge having a chamber, a first porous material received in the chamber and a second porous material received in the chamber, wherein the first porous material receives a quantity of a first liquid composition and wherein the second porous material receives a quantity of a second liquid composition that is different than the first composition; and
   advancing a piston in the chamber to compress the first porous material and the second porous material and urge the first liquid composition and a second liquid composition toward an outlet opening.

35. A method of dispensing a dental composition according to claim 34 and including the act of passing the first liquid composition and a second liquid composition through a mixing element.

36. A method of dispensing a dental composition according to claim 35 wherein the act of providing a cartridge includes the act of providing a mixing element that is received in the chamber.

37. A method of dispensing a dental composition according to claim 36 wherein the act of advancing a piston in the chamber includes the act of compressing the mixing element.

38. A method of dispensing a dental composition according to claim 34 wherein the act of advancing a piston in the chamber includes the act of simultaneously compressing the first porous material and the second porous material to approximately the same extent.

39. A method of dispensing a dental composition according to claim 34 wherein the act of advancing a piston is carried out by moving a plunger of a hand-held applicator.

* * * * *